United States Patent [19]

Castaldi et al.

[11] Patent Number: 4,579,968
[45] Date of Patent: Apr. 1, 1986

[54] PROCESS FOR THE PREPARATION OF OPTICALLY ACTIVE ALPHA-ARYLALKANOIC ACIDS

[75] Inventors: Graziano Castaldi, Briona; Claudio Giordano, Vicenza; Fulvio Uggeri, Codogno, all of Italy

[73] Assignee: Zambon S.p.A., Vicenza, Italy

[21] Appl. No.: 704,406

[22] Filed: Feb. 22, 1985

[30] Foreign Application Priority Data

Feb. 24, 1984 [IT] Italy ............................. 19782 A/84

[51] Int. Cl.$^4$ ............................................. C07C 63/36
[52] U.S. Cl. .................................... 562/490; 560/56; 560/100; 562/465; 562/466; 562/493
[58] Field of Search ............... 562/490, 100, 466, 465, 562/493; 560/56

[56] References Cited

U.S. PATENT DOCUMENTS 4,356,188 10/1982 Pacheco et al. .................... 562/490
4,501,913 2/1985 Giordano et al. .................. 562/490

*Primary Examiner*—Paul J. Killos
*Attorney, Agent, or Firm*—Cushman, Darby & Cushman

[57] ABSTRACT

A process is disclosed for the preparation of optically active alpha-arylalkanoic acids, consisting in the rearrangement of optically active (alpha-haloalkyl)-arylketals and in submitting to hydrolysis the thus obtained esters of alpha-arylalkanoic acids. The rearrangement reaction is carried out under neutral or alightly alkaline conditions, in an aprotic dipolar diluent and in the presence of a protic substance having a high dielectric constant.

9 Claims, No Drawings

PROCESS FOR THE PREPARATION OF OPTICALLY ACTIVE ALPHA-ARYLALKANOIC ACIDS

The present invention relates to a process for the synthesis of optically active alpha-arylalkanoic acids, and more particularly it relates to a process for preparing such acids by means of the rearrangement of suitable ketals under neutral or slightly alkaline conditions, in an aprotic dipolar diluent in the presence of a protic substance having a high dielectric constant, and then submitting to hydrolysis the ester obtained from the rearrangement.

Many alpha-arylalkanoic acids are known due to their pharmaceutical properties (anti-inflammatory agents, analgesics).

Among these, 2-(4-isobutylphenyl)-propionic acid know as Ibuprofen, 2-(3-phenoxyphenyl)-propionic acid known as Fenoprofen, 2-(2-fluoro-4-diphenylyl)-propionic acid known as Flurbiprofen, 2-[4-(2-thienyl-carbonyl)-phenyl]-propionic acid known as Suprofen, 2-(6-methoxy-2-naphth-yl)-propionic acid, whose d isomer is known as Naproxen, and still others may be mentioned.

Another group of alpha-arylalkanoic acids are useful as intermediates for the synthesis of pyrethroid insecticides, among which 2-(4-chlorophenyl)-3-methyl-butyric acid and 2-(4-difluoromethoxyphenyl)-3-methylbutyric acid may be mentioned.

Many alpha-arylalkanoic acids show at least an asymmetry centre, in this case the carbon atom in alpha to the carboxyl, and they exist consequently in the form of two stereoisomers. Often, to one of the two isomers a definitely higher biologioal activity is associated.

A particular evident example is given by 2-(6-methoxy-2-naphthyl)-propionic acid, whose d isomer (Naproxen) has definitely higher pharmacological properties than the l isomer, and the racemic mixture.

Due to this reason, it is useful to have available a stereoselective process leading to the formation of the desired optical isomer in a substantially pure form.

In European patent application No. 81993 to Syntex, claiming the priority of U.S. patent application No. 329,672 filed on Dec. 11, 1981, a stereoselective process is disclosed for preparing optically active ketones of formula

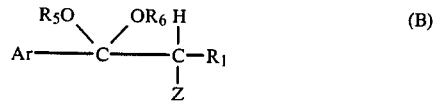

wherein Ar=aryl, R$_1$=alkyl or cycloalkyl, and Z represent a leaving group or a group which can be converted into a leaving group. The preferred leaving groups are halogen atoms, or a group of formula

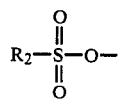

wherein R$_2$=alkyl, cycloalkyl, alkenyl, alkynyl, aryl or arylalkyl. The preparation of the ketones of formula (A) is carried out by reacting an organometallic compound such as an aryl-magnesium halide, with an optically active acyl halide, or by means of similar methods.

According to what reported in European patent application No. 81993, the optically active ketones of formula (A) are then converted into the optically active ketals of formula

wherein Ar, R$_1$ and Z have the above reported meanings, R$_5$ and R$_6$ are are alkyl, aryl or arylalkyl or jointly are a C$_2$-C$_8$ alkylene. From what reported in European patent application No. 81993, it is drawn that the preparation of ketals (B) from ketones (A) is carried out by means of the traditional methods for preparing ketals from ketones (see e.g. the specification thereof from page 29, line 20). The optically active ketones of formula (B) are then converted by rearrangement into the optically active alpha-arylalkanoic acid (or into their ester, orthoester or amide derivatives) of formula

wherein Ar and R$_1$ have the meanings specified above.

As it is clear from the specification of the above mentioned European Patent Application, the rearrangement step is carried out by means of one of the methods known to the filing date of the U.S. priority application (Dec. 11, 1981).

In fact, at page 29, lines 24-foll., it is reported that when in the optically active ketals Z is a halogen, the rearrangement is carried out as discosed in European patent application No. 34871, published Sept. 2, 1981. An alternative process, when Z is a halogen, is the one disclosed in U.K. patent application No. 2042543 published on Sept. 24, 1980 (see Eur. patent application 81993, page 30, line 28-foll.).

When Z is a leaving group of formula R$_2$—SO$_2$—O—, the rearrangement is carried out according to conditions similar or analogous to those described in the paper Tetrahedron Letters 22 (43), 4305-8, (1981), quoted at page 3, lines 30-34 of European patent application No. 81993. Although the aforementioned known methods for rearranging ketals to alpha-arylalkanoic acids are not directly referred to the rearrangement of optically active ketals, they describe the reaction starting from ketals of unspecified isomeric composition.

From the specification of European patent application No. 81993, it is drawn that the known methods described in the above-quoted references can be transferred, without changes, to the rearrangement of optically active ketals of formula (B) (or of the analogous ketals described in Eur. patent application No. 81993). European patent application No. 67698 to Sagami Chemical Research Center published on Dec. 22, 1982 disclosed and claims a process for preparing optically active ketones of formula practically analogous to formula (A) above, and shows how such ketones can be transformed into ketals of formula analogous to the above reported formula (B) (wherein however Z is a sulphonyloxy group only) and the rearranged into alpha-arylalkanoic acids. In our earlier Italian patent application No. 22760 A/82 filed on Aug. 6, 1982 a process has been disclosed for preparing alphaarylalkanoic acid by rearranging (alpha-haloalkyl)-aryl-ketals under neutral or slightly alkaline conditions, and in the presence of a polar protic medium (e.g. water, alcohols, formamide, acetamide ect.). The reaction may be optionally carried out in the presence of an inert diluent such as dimethylformamide, dimethylsulphoxide, toluene, acetone, ect.

In our Italian patent application No. 19930 A/83 filed on Mar. 7, 1983 we have disclosed novel ketals useful to give alpha-aryl-alkanoic acids by rearrangement.

The process disclosed in Italian patent application No. 22760 A/82 shows important advantages over the other rearrangement processes above mentioned.

The main ones of such advantages may be summarized in the fact that the reaction does not require the presence of Lewis acids as catalysts (according to Eur. patent application 34871), in fact the main Lewis acids are halides of heavy metals, which are not compatible with products for pharmaceutical use, and in the fact that the starting products are haloketals, and hence it is not necessary to prepare sulphonyloxy-ketals (according to the paper published on Tetrahedron Letters, or to Eur. patent application 67698).

We have now found and this is the object of the present invention, a process for preparing optically active alpha-arylalkanoic acids, consisting in rearranging (alpha-haloalkyl)-aryl-ketals in neutral or slightly alkaline conditions in the presence of a dipolar aprotic diluent and of a protic substance with high dielectric constant, and in submitting to hydrolysis the ester obtained from the rearrangement reaction.

The process object of the present invention, when compared to the process disclosed in European patent application No. 34871, shows the same advantages of Italian patent application No. 22760 A/82, the main one of them consisting in that the use of heavy-metal salts as rearrangement catalysts is avoided.

When compared to the process disclosed in European patent application No. 81993 (using for the rearrangement the conditions disclosed in Eur. patent application 34871), the process according to the present invention shows the advantage of not using heavy-metal salts as rearrangement catalysts, and in this case the use of heavy metals is a still worse factor, in that the process according to European patent application 81993 directly provides optically active alpha-arylalkanoic acids for direct pharmaceutical use.

Moreover, surprisingly, the process being the object of the present invention provides alpha-arylalkanoic acids with higher optical purity than those obtained by rearraging the same starting products as disclosed in European patent application 81993, i.e. by operating under the conditions as disclosed in European patent application No. 34871. A representative scheme of an aspect of the process being the object of the present invention is shown by the following reactions:

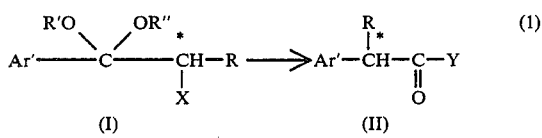

(1)

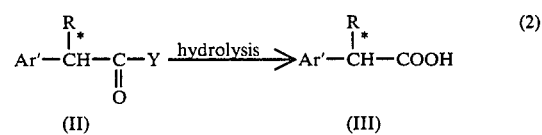

(2)

wherein

Ar' represents an aromatic group comprising (a) a phenyl substituted with one or more substituents selected among halogen atoms, $C_1$-$C_6$ alkyl, $C_1$-$C_4$ alkoxy, $C_2$-$C_4$ alkenyloxy, phenyl, phenoxy, dichlorophenoxy, dichloroanilino, difluoromethoxy, benzoyl, indolyl, dihydropyrrolyl, thienoyl; (b) a naphthyl substituted with one or more substituents selected among halogen atoms and $C_1$-$C_4$ alkoxy; (c) a pyrrolyl substituted with one or two substituents selected among $C_1$-$C_4$ alkyl and $C_1$-$C_4$ alkylphenyl; (d) chlorocarbazolyl; (e) chlorophenyl-benzoxazolyl; (f) thiazolyl substituted with phenyl or chlorophenyl and (g) thienyl;

R' and R", equal to or different from each other, represent a straight or branched $C_1$-$C_{12}$ alkyl or a straight or branched $C_2$-$C_{12}$ alkenyl; or R' and R" together represent a saturated or unsaturated, straight or branched $C_2$-$C_{12}$ alkylene, so as to form with the oxygen atoms and with carbon atom to which they are bonded, a ring of from 5 to 7 atoms;

R represents a straight or branched $C_1$-$C_6$ alkyl, or a $C_3$-$C_7$ cycloalkyl;

X represents a chlorine, bromine or iodine atom;

the asterisk (*) marks the asymmetric carbon atom;

the —CO—Y group represents a group providing a carboxyl group by hydrolysis.

Preferably, the —CO—Y-group represents an ester group of formula —CO—OY', wherein Y' is in general an alkyl when R' and R" are alkyls, or is a substituted alkyl or alkenyl, when R' and R" form together a saturated or unsaturated alkylene; the particular substituent of Y' will depend on the reaction medium.

Specific meanings of the above reported substituents include for Ar': 4-isobutylphenyl, 4-chlorophenyl, 4-difluoromethoxyphenyl, 6-methoxy-2-naphthyl;

for R' and R" individually: methyl or ethyl;

for R' and R" jointly: the groups —CH$_2$—CH$_2$—, CH$_2$—CH$_2$—CH$_2$—, CH$_2$—C(CH$_3$)$_2$—CH$_2$—, —CH$_2$—CH=CH—CH$_2$—;

for X chlorine and bromine;

for R methyl, ethyl, n.propyl, isopropyl.

In a specific embodiment thereof, the invention comprises the preparation of the d isomer of 2-(6-methoxy-2-naphthyl)-propionic acid known as Naproxen according to the above shown reactions (1) and (2), starting from a compound of formula:

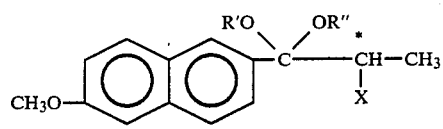

wherein R', R" and X have the hereinabove mentioned meanings and in particular the specific meanings above listed.

The starting products of the process being the object of the present invention, i.e. the optically active ketals of formula (I), are prepared according to per se known methods, and in particular by means of conventional techniques of ketalization of optically active ketones.

Depending on the selected ketalization process type, the configuration can be preserved with respect to the optically active ketone used as the starting product, or the inversion can occur in the configuration.

The optically active ketones necessary for preparing the ketals of formula (I) may be prepared by means of the Friedel-Crafts reaction, as described in European patent application No. 67698, or by means of the Grignard or like reactions, as described in European patent application No. 81993.

Of course, the present invention is not to be intended as limited to the case in which the optically active ketals are prepared as hereinabove briefly mentioned, but it comprises the rearrangement of optically active (alpha-haloalkyl)-aryl-ketals independently from the method by which they are prepared.

As it has previously been briefly mentioned, the process being the object of the present invention consists in a rearrangement step and in a subsequent hydrolysis step. The rearrangement of optically active (alpha-haloalkyl)-aryl-ketals is carried out under neutral or slightly alkaline conditions in an aprotic dipolar diluent in the presence of a protic substance having a high dielectric constant.

The neutral or alkaline conditions are obtained by using organic or inorganic weak bases or buffers.

Examples or useful weak bases are aliphatic or aromatic tertiary amines, alkaline or alkaline-earth salts of weak acids such as sodium bicarbonate, calcium carbonate, potassium acetate, and so on.

The useful aprotic dipolar diluents comprise: dimethyl-formamide, dimethylsulphoxide, hexamethylphosphoric triamide, N-methyl-pyrrolidone, dimethylacetamide, N-methylmorpholine, O-alkylated polyglycols, sulpholane and mixtures thereof.

The protic substances having a high dielectric constant (if they are solid, when dissolved) comprise: water, urea, thiourea, formamide, acetamide, benzamide, phenols, N-methylformamide, N-methyl-acetamide, N,N'-dimethyl-urea and mixtures thereof.

The formamide, due to its good dissolving power for optically active ketals of formula (I), does not require the presence on an aprotic dipolar diluent.

The amount of aprotic dipolar diluent to be used depends on the relative solubility of the ketal, even if in general it is enough to use an amount of diluent sufficient for dissolving about 10% by weight ketal.

Also the amount of protic substance having a high dielectric constant is not critical in that, with reference to the ketal, catalytic amounts may be used ranging up to equimolecular amounts or even in excess. Relatively to the diluent, the protic substance may be present in very variable amounts. Due to practical reasons, it is preferred to use the diluent and the protic substance at high dielectric constant in ratios of from 100:1 to 1:1 volume (or by weight, when one of them is solid), the preferred range being of from 20:1 to 1:1. In general, larger amounts of protic substance increase the reaction rate.

The reaction is normally carried out at temperatures comprised within the range of from 80° to 200° C.

The reaction time depends on several factors, such as the reactivity of the ketal used as starting material, the polarity of the medium, and the reaction temperature, and it may vary from a few minutes up to about 36 hours.

After the end of the rearrangement step, the reaction mixture is treated according to conventional methods, for isolating the compounds of formula (II) so obtained.

The hydrolysis step is then carried out, it too according to conventional methods, mainly by acidic catalysis, the alpha-arylalkanoic acid being thus obtained in high purity.

In a practical embodiment thereof, the process according to the present invention is carried out by introducing into the reactor the optically active ketal, an amount of weak base or of buffet sufficient for ensuring a neutral or slightly alkaline pH an amount of polar aprotic diluent sufficient for at least partially dissolving the ketal, and the protic substance with high-dielectric constant.

The reaction mixture is then heated while being stirred, at a temperature comprised within the range of from 80° and 200° C., and the course of the reaction is followed by means of conventional techniques (GLC, TLC or IR spectroscopy). At the end of the rearrangement reaction, the reaction mixture is poured into water or is diluted the reaction product (the compound of formula [II]) is extracted with a suitable organic solvent and isolated.

The hydrolysis of the compound of formula (II) is then carried out by means of conventional methods, but preferably by acid catalysis. Alternatively, the hydrolysis of the ester may be carried out without isolating it, by adding an aqueous mineral acid to the mixture obtained by the rearrangement reaction.

To the purpose of better illustrating the invention the following Examples are now give.

EXAMPLE 1

A mixture of (S)2-bromo-1,1-dimethoxy-1-(6 methoxy-2-naphthyl)-propane (3.39 g; 10 mmol) (prepared as described in Example 22, page 57, of European patent application No. 81993), calcium carbonate (1 g; 10 mmol), dimethylformamide (12 g) and water (8 g) is stirred at the temerature of 100° C. for 10 hours.

After cooling to 25° C., the mixture is diluted with diethyl ether, and filtered. The organic solution is washed with water, and dried on anhydrous sodium sulphate. The solvent is removed by evaporation under reduced pressure, and the residue is diluted with dimethoxyethane (30 ml) and 10N hydrochloric acid (30 ml.)

The mixture is maintained at 50° C. for 24 hours and is then diluted with water and extracted with diethyl ether. The combined organic phase are washed with water and dried on anhydrous sodium sulphate. After removal of the solvent by evaporation under reduced pressure, (S)-2-(6-methoxy-2-naphthyl)-propionic acid (d isomer) is obtained in an optical purity reflecting the purity of the starting product.

Yield 95%; m.p. 155°–156° C..

EXAMPLE 2

A mixture of (+)(S)2-bromo-1,1-dimethoxy-1-(6-methoxy-2-naphthyl)-propane (3.39 g; 10 mmol), potassium acetate (1.2 g; 12 mmol), N,N-dimethylformamide (14 ml) and of water (8 ml) is heated at 100° C. under stirring. The reaction mixture is worked up as described in example 1 to provide (+)(S)2-(6-methoxy-2-naphthyl)-propionic acid (2.23 g; 9.7 mmol; yield 97%), m.p. 155°–157° C.

EXAMPLE 3

A mixture of (+)(S)2-(1-bromoethyl)-2-(6methoxy-2-naphthyl)-1,3-dioxolane (3.37 g; 10 mmol), potassium acetate (1.2 g; 12 mmol) and formamide (50 ml) is heated under stirring at 170° C.

The reaction mixture is worked up as described in example 1 to provide (+)(S)2-(6-methoxy-2-naphthyl)-propionic acid (yield 52%).

EXAMPLE 4

A mixture of (+)(S)2-(1-bromoethyl)-2-(6-methoxy-2-naphthyl)-1,3-dioxane (3.79 g; 10 mmol), potassium acetate (1.2 g; 12 mmol) and formamide (50 ml) is heated at 170° C. under stirring.

The reaction mixture is worked up as described in example 1 to provide (+)(S)2-(6-methoxy-2-naphthyl)-propionic acid (yield 53%)

EXAMPLE 5

A mixture of (+)(S)2(1-bromoethyl)-2-(6-methoxy-2-naphthyl)-1,3-dioxolane (0.84 g; 2.5 mmol), calcium carbonate (0.3 g; 3 mmol) and formamide (5 ml) is heated at 140° C. under stirring.

The mixture is worked up as described in example 1 to provide (+)(S)2-(6-methoxy-2-naphthyl)-propionic acid (0.172 g; 0.75 mmol; yield 30%), m.p. 154°–155° C.

We claim:

1. Process for the preparation of optically active alpha-arylalkanoic acids, consisting in submitting to rearrangement reaction the corresponding optically active (alpha-haloalkyl)-aryl-ketals in neutral or slightly alkaline conditions in a dipolar aprotic diluent, in the presence of a protic substance having a high dielectric constant, and in submitting to hydrolysis the product obtained from the rearrangement.

2. Process for preparing alpha-aryl-alkanoic acids as claimed in claim 1, applied to the synthesis of (S) 2-(6-methoxy-2-naphthyl)-propionic acid (Naproxen).

3. Process for preparing (S) 2-(6-methoxy-2-naphthyl)-propionic acid as claimed in claim 2, characterized in that as starting product the suitable isomeric form is used of an optically active ketal of formula

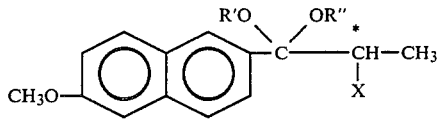

wherein
R' and R", equal to or different from each other, represent a straight or branched $C_2$–$C_{12}$alkyl or a straight or branched $C_2$–$C_{12}$alkenyl; or
R' and R" together represent a saturated or unsaturated, straight or branched $C_2$–$C_{12}$ alkylene, so as to form with the oxygen atoms and the carbon atom to which they are bonded, a ring of from 5 to 7 atoms;
X represents a chlorine, bromine or iodine atom.

4. Process for preparing (S) 2-(6-methoxy-2-naphthyl)-propionic acid as claimed in claim 2, characterized in that as starting product the suitable isomeric form is used of an optically active ketal of formula

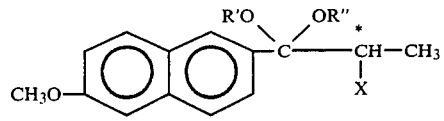

wherein
R' and R" independently represent methyl or ethyl, or together represent a group selected from —$CH_2$—$CH_2$—, —$CH_2$—$CH_2$—$CH_2$—, —$CH_2$—$C(CH_3)_2$—$CH_2$—, —$CH_2$—CH=CH—$CH_2$—;
X represents a chlorine or bromine atom.

5. Process for the preparation of optically active alpha-arylalkanoic acids as claimed in claim 1, characterized in that the rearrangement reaction is carried out at temperatures comprised within the range of from 80° to 200° C.

6. Process for preparing optically active alpha-arylallkanoic acids as claimed in claim 1, characterized in that the reaction medium is made neutral or slightly alkaline by means of the addition of an aliphatic or aromatic tertiary amine, of an alkaline or alkaline-earth salt of a weak acid, or of a buffer.

7. Process for preparing optically active alpha-arylalkanoic acids as claimed in claim 1, characterized in that the dipolar aprotic diluent is selected from dimethylformamide, dimetylsulphoxide, hexamethylphosphoric triamide, N-methyl-pyrrolidone, dimethylacetamide, N-methylmorpholine, O-alkylated polyglycols, sulpholane or mixtures thereof.

8. Process for preparing optically active alpha-arylalkanoic acids as claimed in claim 1, characterized in that the protic substance having a high dielectric constant is selected from water, urea, thiourea, formamide, acetamide, benzamide, phenols, N-methylformamide, N-methylacetamide, N,N'-dimethylurea and mixtures thereof.

9. Process for the preparation of optically active alpha-arylalkanoic acids as claimed in claim 1, characterized in that when the protic substance having a high dielectric constant is formamide, the dipolar aprotic diluent can be omitted.

* * * * *